(12) United States Patent
Shults et al.

(10) Patent No.: US 7,326,577 B2
(45) Date of Patent: Feb. 5, 2008

(54) CELL FIXATION AND USE IN PHOSPHO-PROTEOME SCREENING

(75) Inventors: Keith E. Shults, Nolensville, TN (US); Angel L. Flye, Chapel Hill, TN (US)

(73) Assignee: Esoterix, Inc., Austin, TX (US)

( * ) Notice: Subject to any disclaimer, the term of this patent is extended or adjusted under 35 U.S.C. 154(b) by 511 days.

(21) Appl. No.: 10/918,785

(22) Filed: Aug. 13, 2004

(65) Prior Publication Data

US 2005/0084924 A1    Apr. 21, 2005

Related U.S. Application Data

(60) Provisional application No. 60/512,834, filed on Oct. 20, 2003.

(51) Int. Cl.
*G01N 1/00* (2006.01)

(52) U.S. Cl. .............. 436/176; 435/7.24; 435/40.5; 436/522; 436/18; 436/164; 436/166; 436/172; 436/175; 436/177; 530/388.2

(58) Field of Classification Search ............ 435/7.1, 435/7.24, 40.5; 436/521, 522, 17, 18, 164, 436/166, 172, 175–177; 530/388.2
See application file for complete search history.

(56) References Cited

U.S. PATENT DOCUMENTS

| 4,607,007 A | 8/1986 | Lanier et al. |
| 4,717,655 A | 1/1988 | Fulwyler |
| 5,206,143 A | 4/1993 | Horan et al. |
| 5,422,277 A | 6/1995 | Connelly et al. |
| 5,597,688 A * | 1/1997 | Connelly et al. .......... 435/5 |
| 5,994,089 A | 11/1999 | Siiman et al. |

OTHER PUBLICATIONS

Krutzik et al., Intracellular Phospho-protein Staining Techniques for Flow Cytometry: Monitoring Single Cell Signalling Events (Cytometry Part A 55A-61-70 (Sep. 2003).*
Francis et al., Rapid Singe-Step Method for Flow Cytometric Detection of Surface and Intracellular Antigens Using Whole Blood, Cytometry 25: 58-70 (1996).*
Chow S, et al., Measurement of the MAP kinase activation by flow cytometry using phospho-specific antibodies to MEK and ERK: potential for pharmacodynamic monitoring of signal transduction inhibitors. Cytometry 2001; 46:72-78.
Perez OD & Nolan GP, Simultaneous measurement of multiple active kinase states using polychromatic flow cytometry. Nat. Biotechnol 2002; 20;1551-162.
Jacobberger JW, Flow Cytometric Analysis of Intracellular Protein Epitopes. Immunophenotyping 2000 ; 361-409.
Pizzolo G, et al. Detection of membrane and intracellular antigens by flow cytometry following ORTHO PermeaFix fixation. Leukemia. Apr. 1994;8(4):672-6.

(Continued)

*Primary Examiner*—Gailene Rio Gabel
(74) *Attorney, Agent, or Firm*—Baker & McKenzie LLP

(57) ABSTRACT

A new method of cell fixation using a mild denaturing heat and the fixative PERMIFLOW™ or similar fixative that preserves cell morphology, light scatter profiles, nucleic acid content, cell surface epitopes and unmasks internal epitopes previously not available. The method can be combined with analysis of each of these parameters by flow cytometry and thus has application in drug screening and patient or tumor monitoring protocols.

8 Claims, 8 Drawing Sheets

Treatment at 43°C

OTHER PUBLICATIONS

Francis C & Connelly MC, Rapid single-step method for flow cytometric detection of surface and intracellular antigens using whole blood, Cytometry. Sep. 1, 1996;25(1):58-70.

Baatout S & Cheta N, Permeafix: a useful tool to detect antigens and DNA in flow cytometry, Rom J Intern Med. Jan.-Dec. 1997;35(1-4):133-5. Abstract.

Murray M, et al., ORTHO Permeafix fixation is not suitable for the flow cytometric detection of nuclear terminal transferase in acute myloid leukemia cells. Leukemia. Jan. 1995;9(1):226-8. Abstract, Comment.

Metso T, et al., Identification of intracellular markers in induced sputum and bronchoalveolar lavage samples in patients with respiratory disorders and healthy persons. Respir Med. 2002 Nov. 2002;96(11):918-26.

Hubert P, et al., Analysis by Flow Cytometry of Tyrosine-Phosphorylated Proteins in Activated T-Cell Subsets on Whole Blood Samples. Cytometry 29:83-91(1997).

Janknecht R, et al., Rapid and efficient purification of native histidine-tagged protein expressed by recombinant vaccinia virus. Proc. Natl. Acad. Sci. USA, 88:8972-8976(1991).

Knapp W, et al., Flow Cytometric Analysis of Cell-surface and Intracellular Antigens in Leukemia Diagnosis. Cytometry 18:187-198(1994).

Maulon L, et al., T-Cell Receptor Signaling Pathway Exerts a Negative Control on Thrombin-Mediated Increase in [Ca2+]l and p38 MAPK Activation in Jurkat T Cells: Implication of the Tyrosine Kinase p56Lck. Blood 91(11)4232-4241, 1998.

Krutzik P, et al., Intracellular Phospho-protein Staining Techniques for Flow Cytometry: Monitoring Single Cell Signaling Events. Cytometry Part A 55A:61-70(2003).

Sindermann J, et al., A simple method for the flow cytometric analysis of intracellular antigens in whole smooth muscle cells: quantification of cyclin-dependent kinase 2. Journal of Immunological Methods 202:205-212(1997).

Verdier M, et al., Optimization of Cell Permeabilization for Multiparametric Flow Cytometric Analysis with Lectin Staining. Cytometry 41:55-61(2000).

Wenisch C, et al., Antifungal susceptibility testing of fluconazole by flow cytometry correlates with clinical outcome. J Clin Microbiol. 39(7):2458-2462(2001). Abstract.

Far D, et al., Immunofluorescent quantification of tyrosine phosphorylation of cellular porteins in whole cells by flow cytometry. Cytometry 15(4):327-34(1994). Abstract.

* cited by examiner

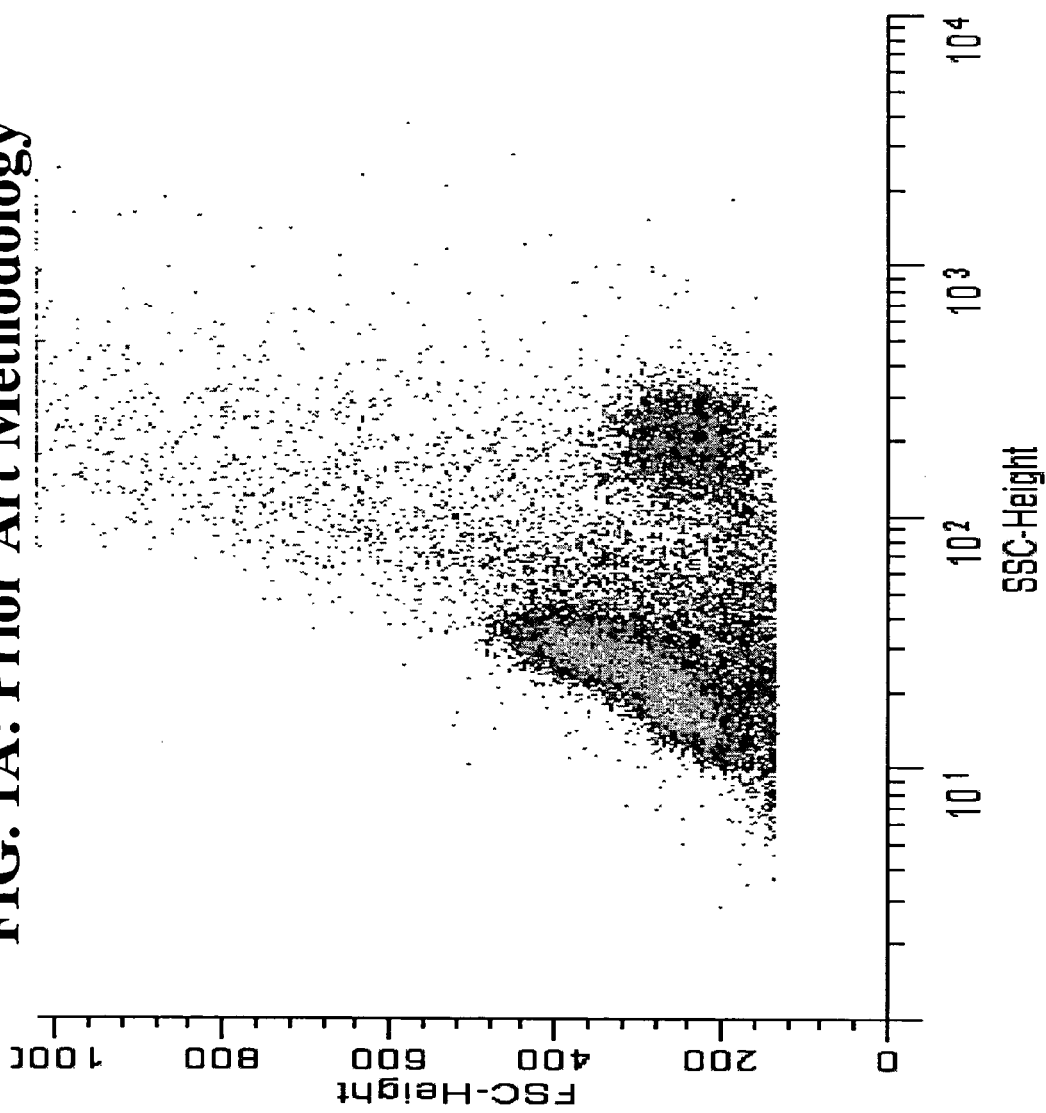

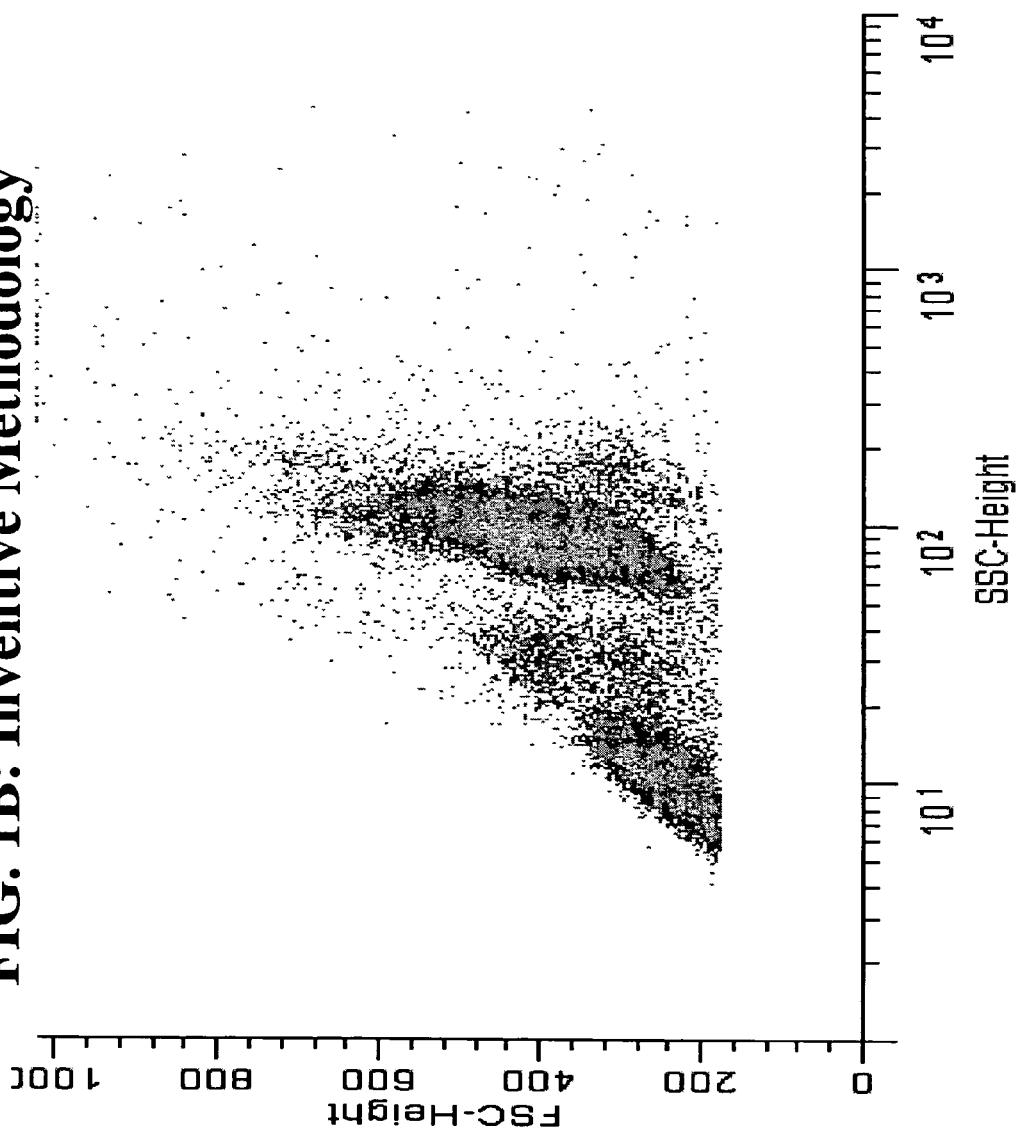

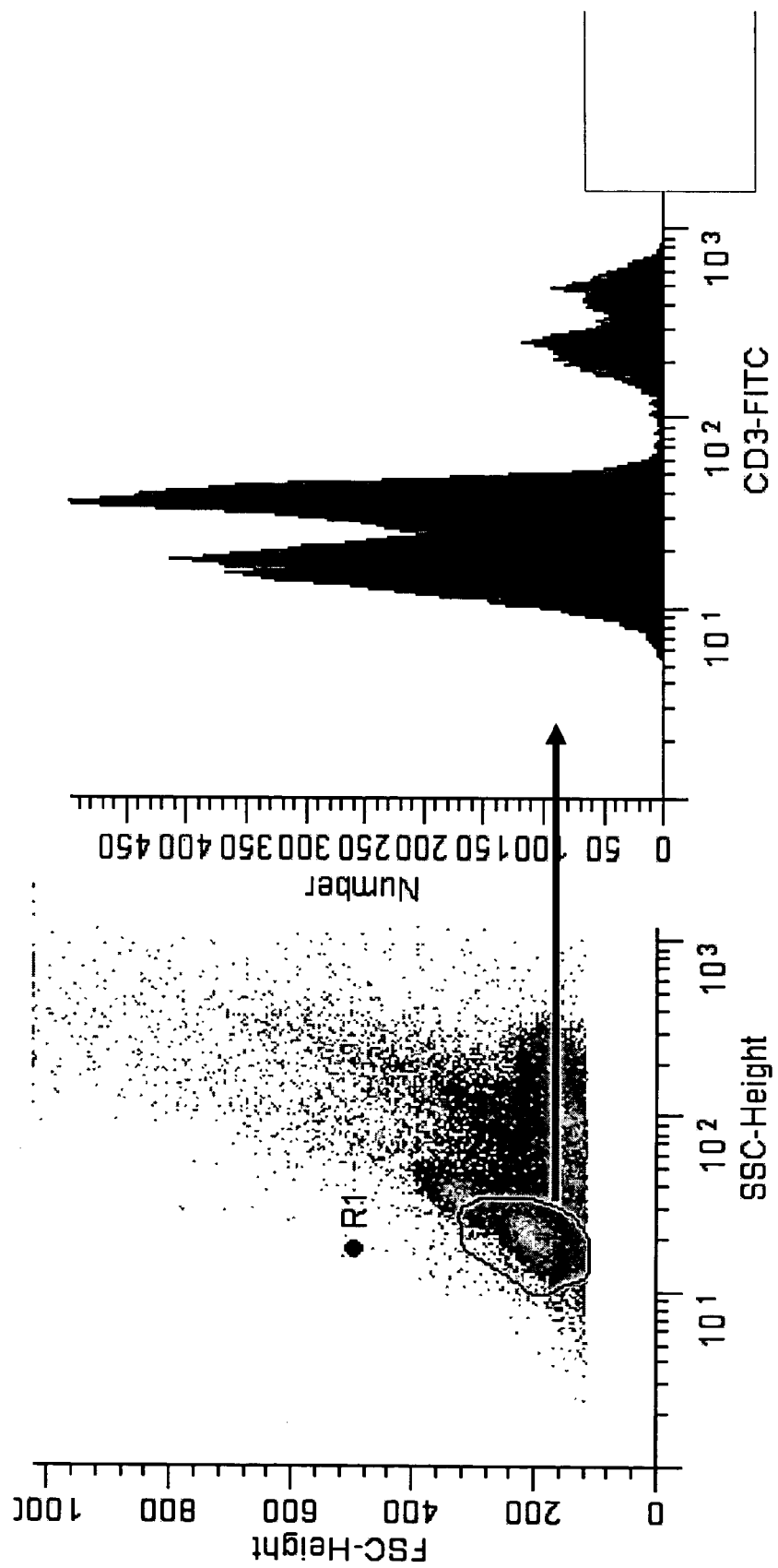
FIG. 2A: Prior Art Methodology

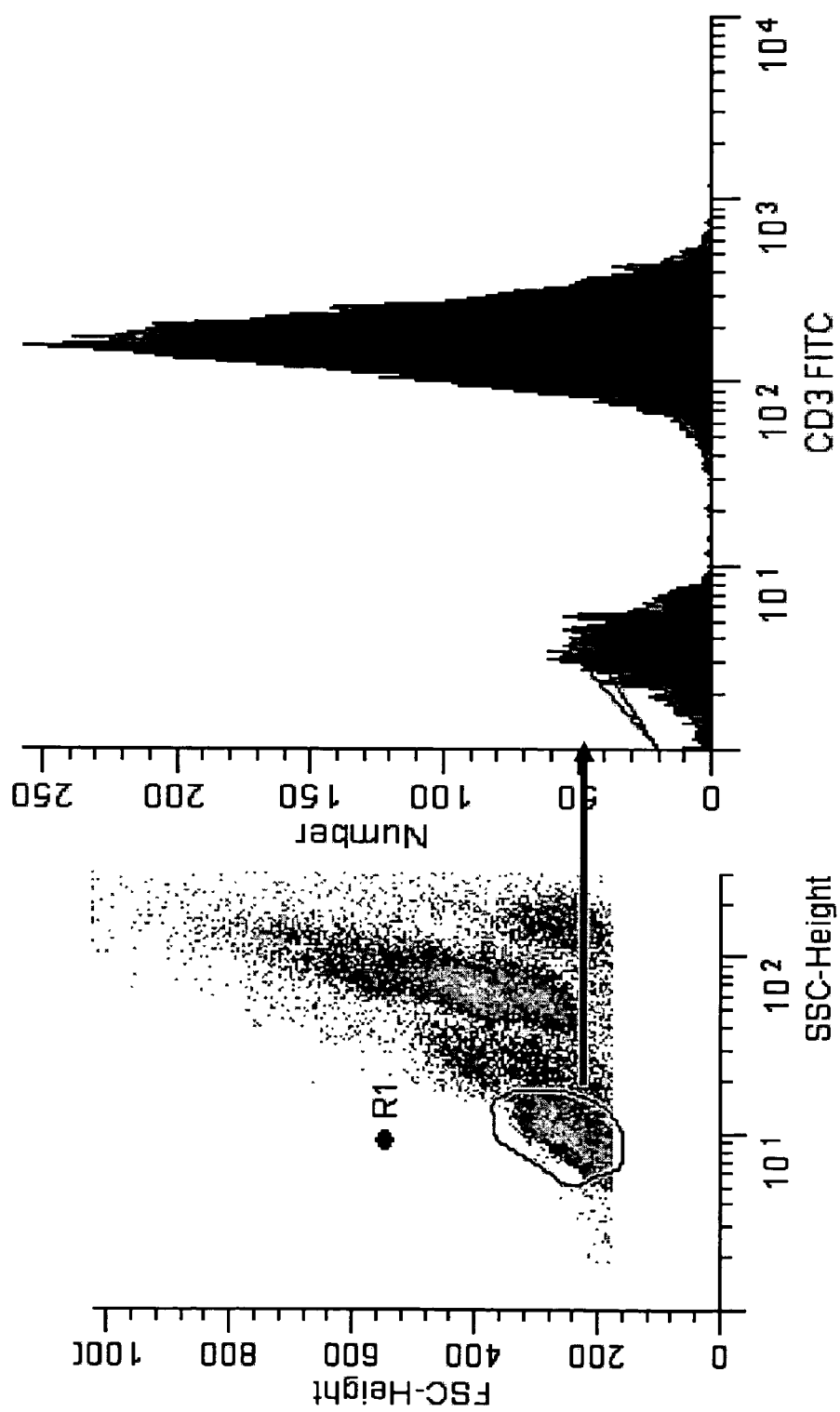
FIG. 2B: Inventive Methodology

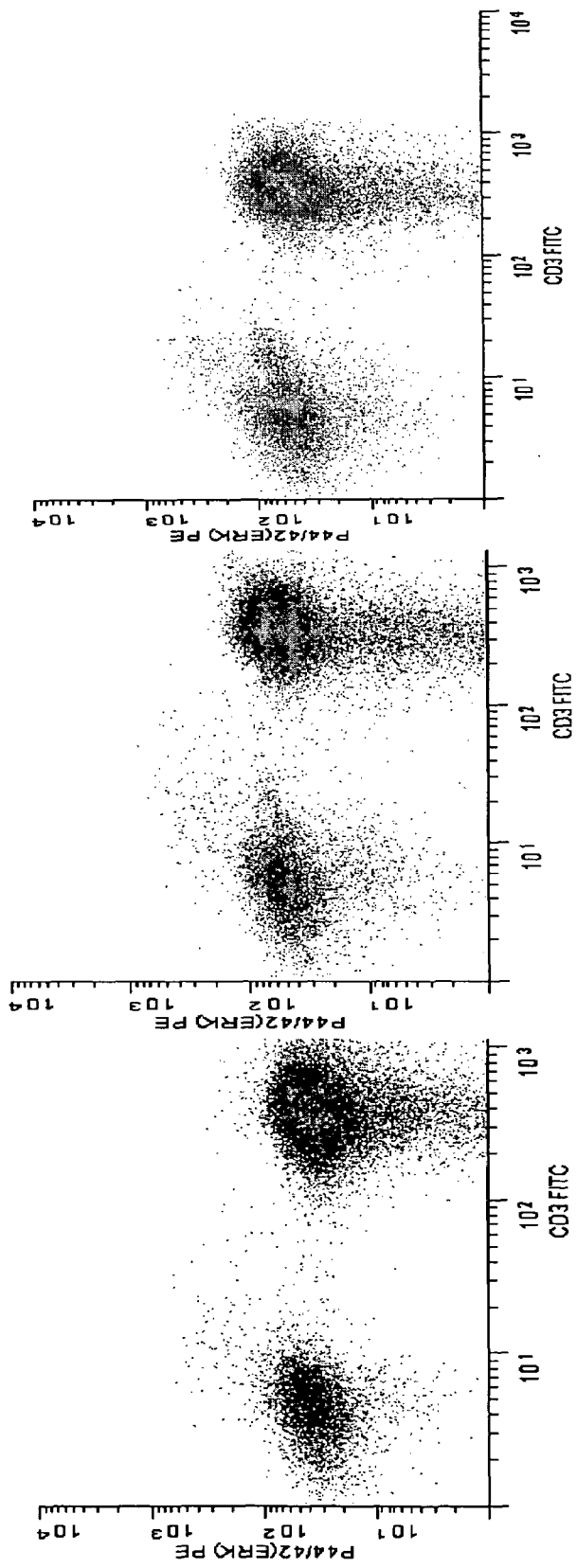

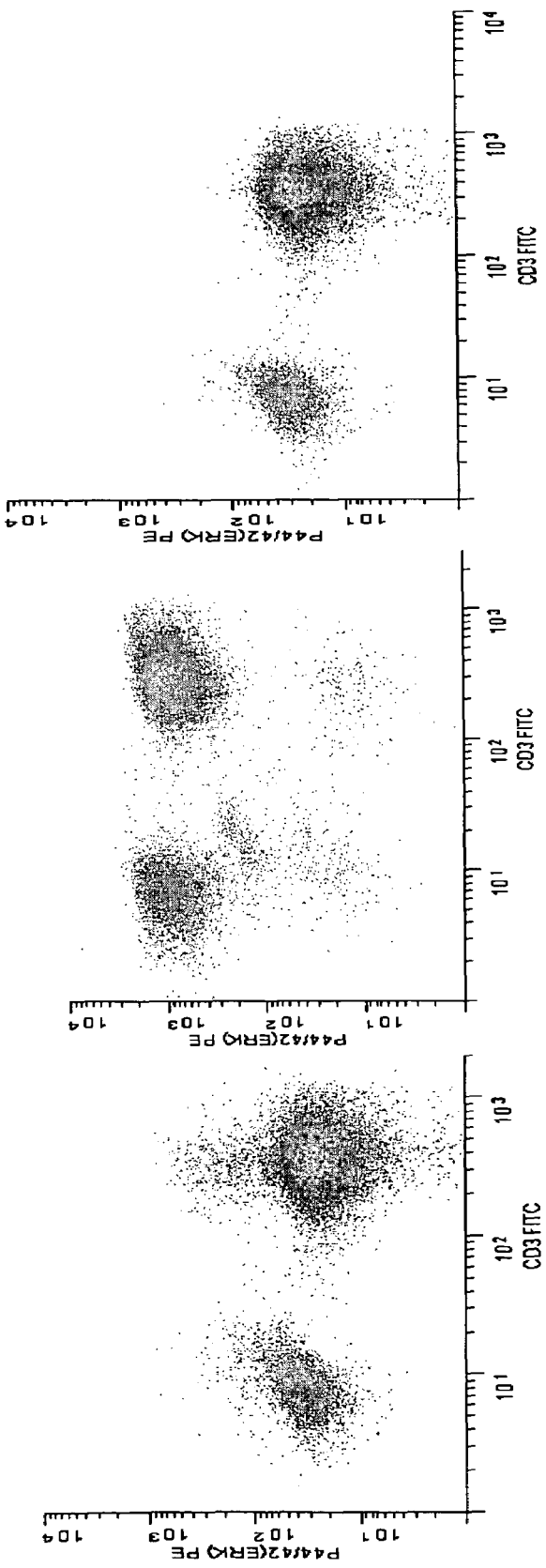
FIG. 3B: Treatment at 43°C

CELL FIXATION AND USE IN PHOSPHO-PROTEOME SCREENING

PRIOR RELATED APPLICATIONS

This application claims the benefit of U.S. Provisional Application No. 60/512,834, filed Oct. 20, 2003.

FEDERALLY SPONSORED RESEARCH STATEMENT

Not applicable.

REFERENCE TO MICROFICHE APPENDIX

Not applicable.

FIELD OF THE INVENTION

The invention relates to a new method of fixing cells. The resulting fixed cells have retained immuno-detectable surface antigens, intracellular antigens, cell morphology, light scattering properties, and nucleic acid profiles. Thus, the cells can be used in a variety of applications previously not possible because prior art fixation methods degraded one or more of these properties. Applications of the new fixation method include drug screening methods. For example, it is possible to screen whole blood for drugs that affect the signal transduction pathways, for example MAP KINASE pathways. Other applications include diagnostic uses such as typing tumors or monitoring tumor responsiveness to a treatment regime.

BACKGROUND OF THE INVENTION

The detection of phosphorylated proteins holds great promise in delineating many of the signal transduction pathways that occur in normal and diseased cells. The possibility of studying the phospho-proteome as an indicator of the drug efficacy is gaining popularity in the pharmaceutical industry, in part due to the disappointing results obtained using standard genomic approaches.

Classic analysis of cell signaling pathways uses cell lines incubated in the presence and/or absence of an activator or inhibitor. Proteins are then extracted and analyzed by Western blot using one or more anti-phospho-protein antibodies. Unfortunately, this approach is time consuming, expensive and not amenable to high throughput screening.

Flow cytometry has advantages over Western blot, in that specific subsets of cells can be targeted due to reproducible light scatter profiles obtained when cells are interrogated by laser light combined with various fluorescent antibodies. Further, flow cytometry can be used to detect intracellular phospho-epitopes. In comparing cytometric detection to Western blots, several other advantages surface, including, but not limited to: 1) a large dynamic range of data collection (typically 10,000 fold), 2) rapid protocols that take 2 hours, not 2 days, 3) simultaneous analysis of multiple epitopes in the same cell, and 4) the possibility of quantitation in a single cell.

The literature describing cytometric detection of phospho-epitopes is limited to two seminal papers. In the first paper, Chow, et al. (1) described a technique for whole blood or isolated cells that detected inhibition in the MAP kinase pathway using phospho-specific antibodies to MEK/ERK. The authors list the destruction of surface epitopes and poor light scatter resolution as detrimental to the analysis. In a more "proof of principle" sense, Perez, et al. (2) demonstrated the detection of multiple epitopes using multiple fluorochromes on isolated lymphocytes and cell lines.

In both papers, the authors allude to the fact that if a fixation technique could be devised that maintained surface epitopes together with resolvable light scatter, the use of cytometry would be more broadly applicable. However, to date no satisfactory fixative has been found that maintains both surface and intracellular epitopes, light scatter properties of the cell, and DNA profiles.

Current fixatives revolve primarily around alcohol and formaldehyde/paraformaldehyde (3). Alcohols dehydrate the cell allowing immediate internal access, but are detrimental to most surface epitopes and cause the cells to aggregate. The crosslinkage of proteins is the attractive feature of paraformaldehyde fixatives. However, this feature denies access to proteins in their native state and is detrimental to DNA dyes.

What is needed in the field is a fixative technique that 1) maintains easily resolvable light scatter patterns, 2) preserves surface epitopes, 3) preserves intracellular epitopes, and 4) allows DNA content analysis if so desired. An added benefit would accrue if the fixative could be used on whole blood or bone marrow due to its ability to lyse mature red blood cells (RBC).

The fixative described by Connelly (4a) is the best single step fixative and permeation agent discovered to date (see e.g., reference (8) stating that "Best results were obtained using a commercial reagent Ortho PermeaFix (OPF) for flow cytometry"). It is called Ortho PERMEAFIX™, although that product has been replaced with a new product called PERMIFLOW™ (INVIRION, INC.™ MI). OPF and its variants are well described in U.S. Pat. No. 5,422,277 and U.S. Pat. No. 5,597,688. Preferred fixatives comprised 0.756%-0.85% formaldehyde, 25.4-30 mM DNBS, 6.9-6.92% DMSO and 0.086-0.095% TWEEN™ 20 detergent, although many variations are described.

OPF fixation is asserted to have "maintained the morphology of lymphoid cells with minimal cellular distortion and scatter changes, and only slightly modified cell surface immunoreactivity." (4a). In fact, Connelly has successfully applied this fixative to the detection of both surface and intracellular antigens (4b, 5), and a particular benefit is that an additional red blood cell (RBC) lysing reagent was not required because RBC lysis occurred upon resuspension of OPF-treated whole blood samples in isotonic solution. Others have shown that unlike most other fixatives, OPF is also compatible with DNA staining (6).

The inventors of OPF specifically teach that "the temperatures maintained during such [fixation] incubation are generally 0° C. to about 37° C., with room temperature preferable" (5). In contrast to the patent, however, a scientific publication by the Connelly group (4a) states that morphology is improved at 4° C. over a room temperature fixation. In fact, most cell preparation techniques for flow cytometry require fixation on ice or at most room temperature, because the lower temperature is believed to be required to maintain the cell's metabolic state until fixation, and to maintain cell morphology during and after fixation.

Unfortunately, many antigens cannot be detected after room temperature fixation (see, e.g., (7) and the results described herein). Thus, an improved fixative method is needed in the art.

SUMMARY OF THE INVENTION

The present invention provides an improved cell fixation method that preserves surface epitopes and allows improved access to internal epitopes, while also preserving cell morphology, light scatter profiles and nucleic acid content. Generally speaking, the method involves using the known single step fixation and permeation reagents known in the literature as PERMEAFIX™ or PERMIFLOW™, but at mild denaturation temperatures previously thought to be detrimental to cell morphology and subsequent analysis by flow cytometry.

The invention allows the detection of internal epitopes, such as the phospho-epitopes relevant to signal transduction cascades, which were not detectable with the prior art techniques using these fixatives on ice or at room temperature. Thus, the fixation method can now be used as the basis of techniques of drug screening using whole blood samples, or patient monitoring techniques, whereby whole blood is analyzed according to cell type (because cell morphology is well maintained allowing the cells to be gated according to their light scatter profiles), surface antigens and DNA content (both of which are well preserved by the technique), as well as internal phospho-epitopes, such as the phosphorylated ERK, MEK, MAPK, MAP2K, MAP3K, etc. cascade proteins.

Tissues that can be studied according to the inventive method include whole blood and bone marrow, as exemplified herein. Tissues and cells obtained by biopsy, such as tumor samples, as well as various cell lines can also be employed in the methods.

Thus, drugs can be now screened for their effect on signal transduction cascades and DNA content in a variety of cell types simultaneously. The same techniques can be used to monitor a particular patient's response to a treatment regime, and can be used to monitor the response of particular tumor types to a given treatment. Importantly, whole blood can be used without prior separation of cell types and without prior removal of RBC. Thus, sample collection and analysis is facilitated, allowing the easy screening of large numbers of samples in an efficient way.

Other applications of the new method of cell fixation include: 1) Simultaneous study of cell cycle phases and phospho-epitopes in cell lines exposed to stimulators/inhibitors/small molecule drugs for purposes of drug discovery. 2) Studies comparing matched normal/diseased bone marrow in which one wishes to compare the signal transduction cascades following stimulation with growth factors. 3) Toxicology/safety studies performed on bone marrow elements to delineate the effects of compounds on the signal transduction molecules.

BRIEF DESCRIPTION OF THE DRAWINGS

FIGS. 1A and 1B. Whole blood light scatter patterns. The pattern in FIG. 1A. is obtained the using the prior art lysis technique of Chow (1) using 100 µl whole blood. The pattern in FIG. 1B is obtained using the same donor and the lysis method of the invention (note the recognizable 3 part pattern).

FIGS. 2A and 2B. Comparison of surface epitopes. The pattern in FIG. 2A is the prior art technique of Chow (1). The Pattern in FIG. 2B is obtained using the same donor and the method of the invention (note the resolvable lymphocyte population—circled and labeled R1).

FIGS. 3A and 3B. Comparison of internal epitopes. In FIG. 3A the cells were activated with PMA and stained with anti-CD3. The cells in the third panel were co-incubated with the MEK inhibitor UO126. The cells were then fixed at room temperature and stained with anti-phospho-ERK. In FIG. 3B, the same activation and staining reagents were used; however, the fixation took place at 43° C. (note the detection of phospho-ERK occurring only at the higher temperature).

DESCRIPTION OF EMBODIMENTS OF THE INVENTION

Figure 4:
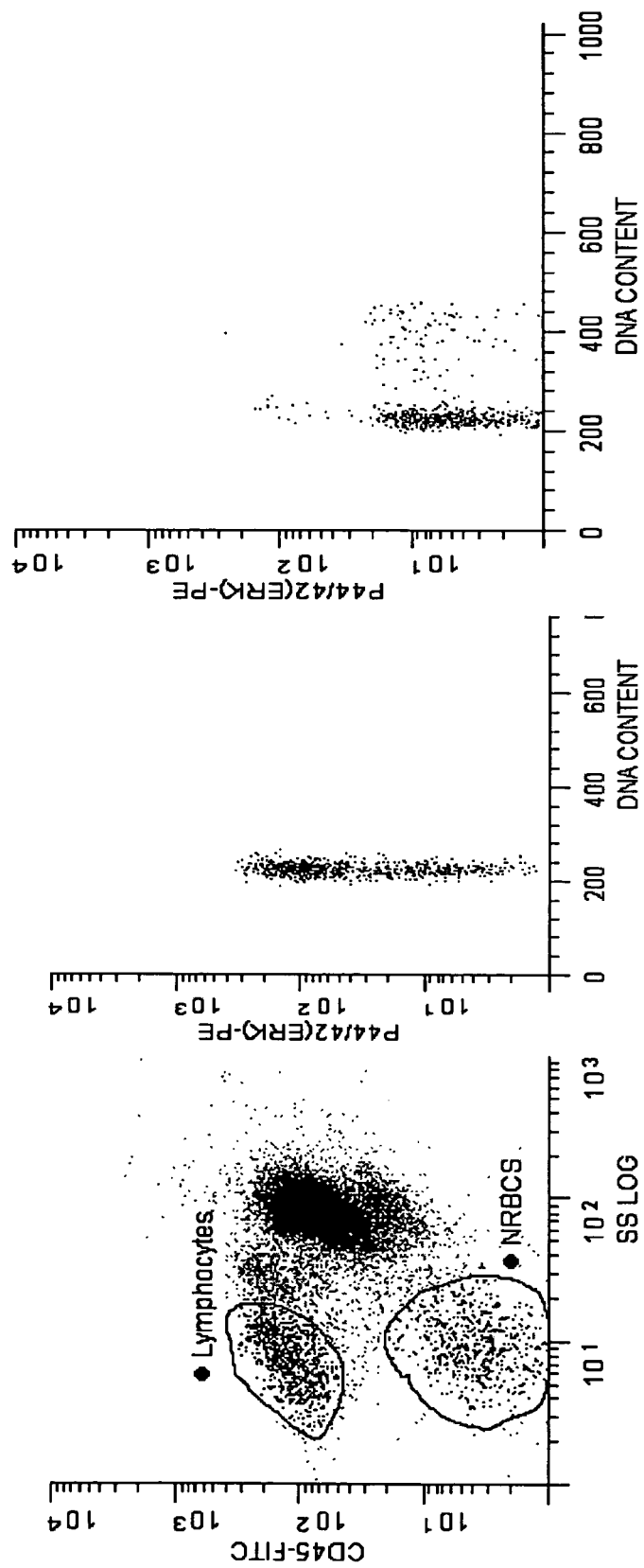
FIG. 4. Studies on normal bone marrow. Whole marrow was activated with PMA and stained with anti-CD45, fixed according to the invention and then stained with anti-phospho-ERK and the DNA dye DRAQ5. As depicted on the left, all marrow populations are resolvable. The cells in the upper circle are lymphocytes that activated nicely as evidenced by the phospho-ERK signal. The cells in the lower circle are nucleated red blood cells (NRBCs) that lack the RTK receptor necessary to activate ERK. The DNA content and phospho-ERK staining of the lymphocytes are shown in the middle panel while the DNA content and phospho-ERK straining of the NRBC are shown in the third panel.

The present invention provides an improved cell fixation method using PERMEAFIX™ or PERMIFLOW™ at mild denaturation temperatures that were previously thought to be detrimental to cell morphology and thus subsequent analysis by flow cytometry. The invention is exemplified with respect to the commercially available fixative known as PERMIFLOW™. However, as taught in the patents describing this product, some variation on the basic recipe nevertheless provides acceptable fixatives (5).

Acceptable fixatives for use with the invention are defined herein as fixatives that allow both cell fixation and permeation, while retaining cell surface morphology and DNA and RNA content, sufficient to allow separation of cells based on light scatter, surface epitopes and/or nucleic acid content. An acceptable fixative according to the invention contains the following:

i) a first fixative compound selected from the group consisting of 2,4-dinitrobenzene sulfonamides, dinitrophenols, 3,5-dinitrosalicylic acid, 2,4-dinitrobenzoic acid, 5-sulfosalicylic acid, 2,5-dihydroxy-1,4-benzene disulfonic acid, 3,5-dinitrobenzoic acid, 8-hydroxyquinoline-5-sulfonic acid, 4-nitrophenol, 3,5-dinitrosalicylaldehyde, 3,5-dinitroaniline, paratoluene sulfonic acid, 2-mesitylene sulfonic acid, 2-(trifluoromethyl) benzoic acid, and 2,4-dinitrobenzene sulfonic acid;

(ii) an alcohol-free, second fixative compound selected from the group consisting of formaldehyde, paraformaldehyde, glutaraldehyde, acrolein, glyoxal, malonaldehyde, diacetyl, polyaldehydes, carbodiimides, diisocyanates, diazonium compounds, diimido esters, diethylpyrocarbonate, maleimides, benzoquinone, and metallic ions;

(iii) a fusogenic compound selected from the group consisting of dimethylsulfoxide, sulfolane, 1-methyl-2-pyrrolidinone, polyethylene glycol, and ethyleneglycol; and (iv) a zwitterionic or non-ionic surfactant.

In one embodiment, the fixative is 14% (v/v—all measurements are v/v unless indicated otherwise) dimethyl sulfoxide (DMSO, SIGMA CHEMICAL CO.™); 0.14% (w/v) polyoxyethylene sorbitan monolaurate (TWEEN™ 20, ALDRICH CHEMICAL COMPANY™); 39.2 mM 2,4-dinitrobenzene sulfonic acid sodium salt (DNBS, ALDRICH CHEMICAL CO.™); 1.51% formaldehyde (Ultrapure 10% EM grade, POLYSCIENCES INC.™); 1.470 mM $KH_2PO_4$; 2.683 mM KCl; 8.058 mM $Na_2HPO_4$ and 67 mM NaCl, pH 7.4. However, lower levels of formaldehyde (<0.8%) are strongly preferred, as reducing background fluorescence and better preserving nucleic acid content.

Particularly preferred embodiments comprise 0.75-0.85% formaldehyde, 25-30 mM DNBS, 6.8-7% DMSO and 0.08-0.1% TWEEN™ 20 detergent. The most preferred fixative is PERMIFLOW™.

Mild denaturing temperatures according to the invention are those temperature that improve access to internal antigens, without compromising cell morphology, surface antigens or nucleic acid content. Preferred temperatures range from 39 to 43° C., and especially 40, 41, or 42° C. and most preferred 43° C.

EXAMPLE 1

Fixative Method

Figure 5:
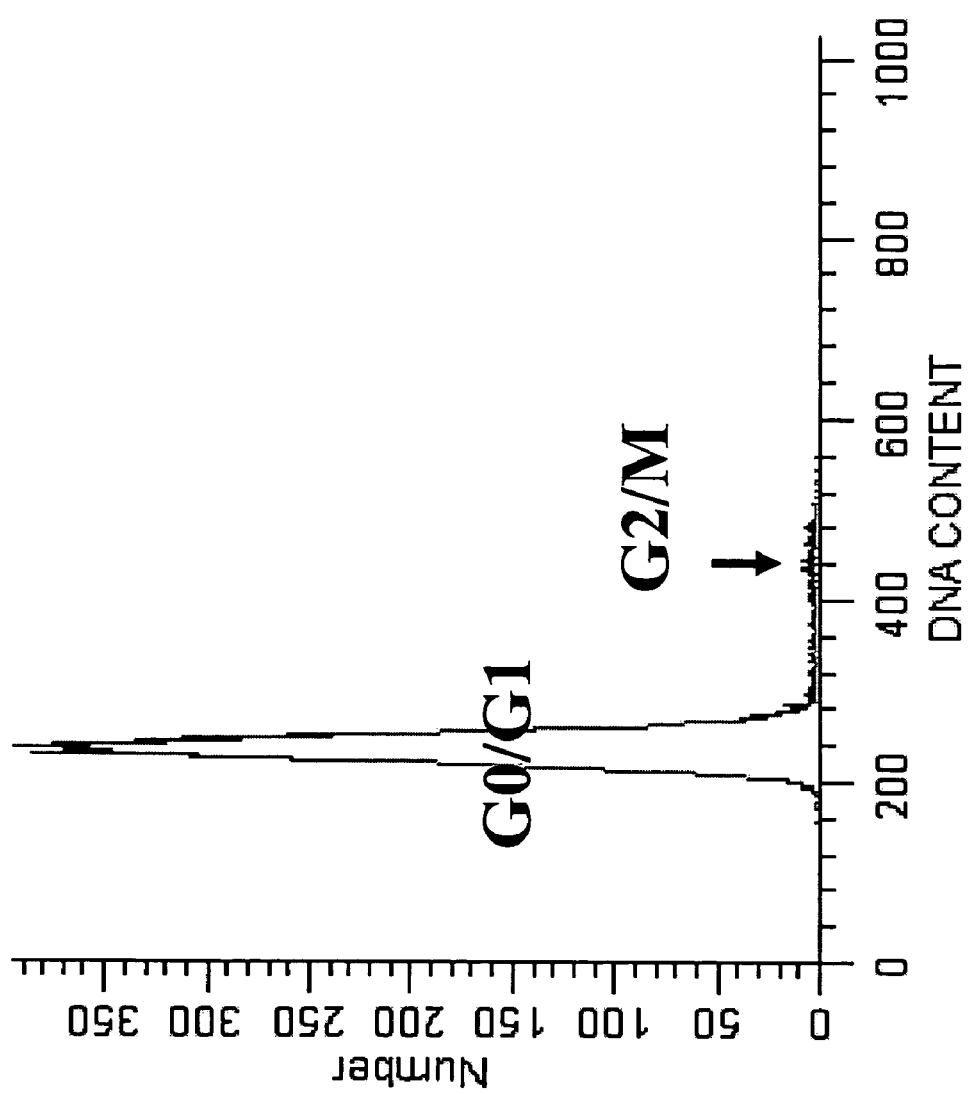
FIG. 5. The DNA histogram shows the ability to study all phases of the cell cycle.

For analysis of whole blood by flow cytometry, including evaluation based on light scatter, surface epitopes, internal epitopes, and nucleic acid content, the following protocol was employed:

1. Sterilely place 100 µl of whole blood or 50 µl of whole marrow in each of the 2 tubes for each antibody combination desired.
2. Sterilely add 2 ml of standard culture media to each tube and vortex briefly to mix.
3. Add 4 times saturating amount (as determined by titration) of desired anti-surface-epitope antibodies to each tube.
4. Add any growth factors or inhibitors required by study at this point. In this case, activation of the MAP Kinase cascade was studied, requiring stimulation of the cells with PMA.
5. Add 50 µl of stock PMA solution to the "PMA" tubes and vortex briefly to mix. Start timer immediately and place tubes in 37° C., 5% $CO_2$ incubator for the exact pulse time required (either determined by previous studies, antibody certificate of analysis, or other literature; e.g., for phospho-ERK a 10 minute pulse is used). Note, the timing must be precise to obtain the best results.
6. Immediately after incubation, spin the tubes at 400 RCF for 5 minutes. Decant the supernatant and disperse the pelleted cells by gently raking.
7. Immediately add 3 ml of pre-prepared room temperature PERMIFLOW™ to each tube. Cap and vortex to mix. Place each tube in a 43° C. water bath for 1 hour, vortexing again at a 30-minute interval.
8. Spin the cells again, decant the supernatant, and disperse the pellet as above. Add 2 ml of cold PBS+2% FCS to each tube and place in dark at room temperature for at least 10 minutes and up to 1 hour. Spin and decant the supernatant as above.
9. Wash cells 1 more time with PBS+2% FCS.
10. Add 100 µl of prepared anti-phospho-epitope antibody (use a saturating amount prepared in PBS+3.4% BSA). Vortex briefly and place in the dark at room temperature for 30 minutes.
11. Wash the cells twice in PBS+2% FCS. Decant and disperse by raking.
12. Add 50 µl of prepared secondary antibody, as required to each tube. Vortex briefly and incubate at room temperature in the dark for 30 minutes.
13. Repeat the wash of step 11 and re-suspend the cell pellet in 1 ml of PBS+2% FCS. If DNA analysis is required, resuspend cell pellet in 1 ml of saturating DNA dye and a balanced salt solution.
14. Tubes are ready for data collection after incubation is complete. We have used the Epics XL or FACS Calibur Flow cytometer herein, but any properly quality controlled flow cytometer that satisfies established windows of analysis can be used. Ensure that the laser excitation line or lines and filter configurations are correct for the excitation and detection of all fluorescence labels used in assay. The analysis that is actually performed will vary depending on the experiment being performed, which of the cellular parameters are of interest, and the actual labels employed.
15. Collect 30,000 ungated events.
16. Analyze data in WinList and Excel or equivalent for the percentage expression of phospho-epitope in "PMA" tubes compared to "No PMA" tubes. The results are shown in FIGS. 1 through 5.

EXAMPLE 2

Heat Fixation

The use of OPF or PERMIFLOW™ as a fixative, permeation and lysis reagent was introduced in the original publications describing the product (4a, 4b, 5). However, to our knowledge this reagent has not been previously used for the detection of phospho-epitopes. Chow (1) and Perez (2) have studied phospho-epitopes by flow cytometry, but with the older paraformaldehyde/methanol based fixatives. The use of paraformaldehyde and methanol fixation is known to be detrimental to many surface epitopes and is emphasized in both the Chow (1) and Perez (2) articles.

The use of heat in antigen retrieval systems in immunohistochemistry is well documented, but is typically not used in flow cytometry because researchers desire to slow down or stop metabolic activity and preserve intact cell morphology and status during fixation. Therefore, fixation is typically performed on ice or at room temperature. We have compared room temperature fixation to 43° C. fixation using the same PERMIFLOW™ reagent, and the results were surprisingly quite strikingly different (FIG. 3). Antigens masked at the lower temperature became available at the higher temperature, yet cell morphology remained intact. Further, we have shown that PERMIFLOW™ withstands the heat necessary for phospho-epitope detection.

Preferably, the fixation temperature is 43° C. At higher temperatures, there is a certain amount of signal and morphological decay. However, the temperature must be high enough to allow a certain level of mild denaturation. Thus, useful temperatures range from 39-43° C.

For the technique to be used with the least manipulation, the ability to analyze whole blood or marrow is essential. The primary sample in clinical trials is anticipated to be blood samples with the inhibitor onboard. We have tested all anti-coagulants (EDTA, ACD, sodium Heparin) and obtained the same scatter patterns using our technique. The Chow technique (DI water followed with 10×PBS) consistently destroyed polymorphonuclear cells (PMNs) and did not allow separation of lymphocytes/monocytes.

The following citations are incorporated by reference herein.

(1) Chow S, et al., Measurement of the MAP kinase activation by flow cytometry using phospho-specific antibodies to MEK and ERK: potential for pharmacodynamic monitoring of signal transduction inhibitors. Cytometry 2001; 46:72-78.

(2) Perez O D & Nolan G P, Simultaneous measurement of multiple active kinase states using polychromatic flow cytometry. Nat. Biotechnol 2002; 20;1551-162.

(3) Jacobberger J W, Flow Cytometric Analysis of Intracellular Protein Epitopes. Immunophenotyping 2000 ; 361-409.

(4a) Pizzolo G, et al. Detection of membrane and intracellular antigens by flow cytometry following ORTHO PermeaFix fixation. Leukemia. 1994 April;8(4):672-6.

(4b) Francis C & Connelly M C, Rapid single-step method for flow cytometric detection of surface and intracellular antigens using whole blood, Cytometry. 1996 Sep 1;25(1):58-70.

(5) U.S. Pat. No. 5,422,277 and U.S. Pat. No. 5,597,688

(6) Baatout S & Cheta N, Permafix: a useful tool to detect antigens and DNA in flow cytometry, Rom J Intern Med. 1997 January-December;35(1-4):133-5. Related Articles, Links (7) Murray M, et al., ORTHO Permeafix fixation is not suitable for the flow cytometric detection of nuclear terminal transferase in acute myloid leukemia cells. Leukemia. 1995 January;9(1):226-8.

(8) Metso T, et al., Identification of intracellular markers in induced sputum and bronchoalveolar lavage samples in patients with respiratory disorders and healthy persons. Respir Med. 2002 November;96(11):918-26.

What is claimed is:

1. A method of fixing cells, comprising,
   fixing the cells at mild denaturation conditions of about 43° C. using a fixative which comprises 0.75%-0.85% formaldehyde, 25-30 mM DNBS, 6.8-7% DMSO, and 0.085-0.095% TWEEN™ 20 detergent.

2. The method of claim 1, wherein said mild denaturation condition is 43° C. using PERMIFLOW.™

3. A method of determining a response to a test reagent comprising:
   a. treating a subject with at least one test reagent and collecting a cell sample from the subject,
   b. staining at least one cell surface epitope in the cell sample with an anti-surface epitope antibody;
   c. fixing the cell sample at about 43° C. with a fixative comprising 0.75% -0.85% formaldehyde, 25-30 mM DNBS, 6.8-7% DMSO and 0.085-0.095% TWEEN™ 20 detergent;
   d. optionally lysing any red blood cells in the cell sample under isotonic conditions;
   e. staining the cells having at least one intracellular phospho-epitope with an anti-phospho-epitope antibody;
   f. staining nucleic acid;
   g. analyzing the cells in flow cytometry by light scatter, anti-surface epitope antibody binding, anti-phospho-epitope antibody binding and nucleic acid stain,
   h. comparing the cells against control cells not treated with said test reagent, whereby differences in the anti-phospho-epitope antibody binding indicate a response to said test reagent.

4. The method of claim 3 wherein the fixation is performed at 43° C. using PERMIFLOW™.

5. The method of claim 3, wherein the cell sample is whole blood.

6. The method of claim 3, wherein the cell sample is bone marrow cells.

7. The method of claim 3, wherein the cell sample is tumor cells.

8. The method of claim 3, wherein the anti-phospho-epitope antibody is a mitogen activated protein (MAP) KINASE CASCADE antibody.

* * * * *